Figures 1, 2:
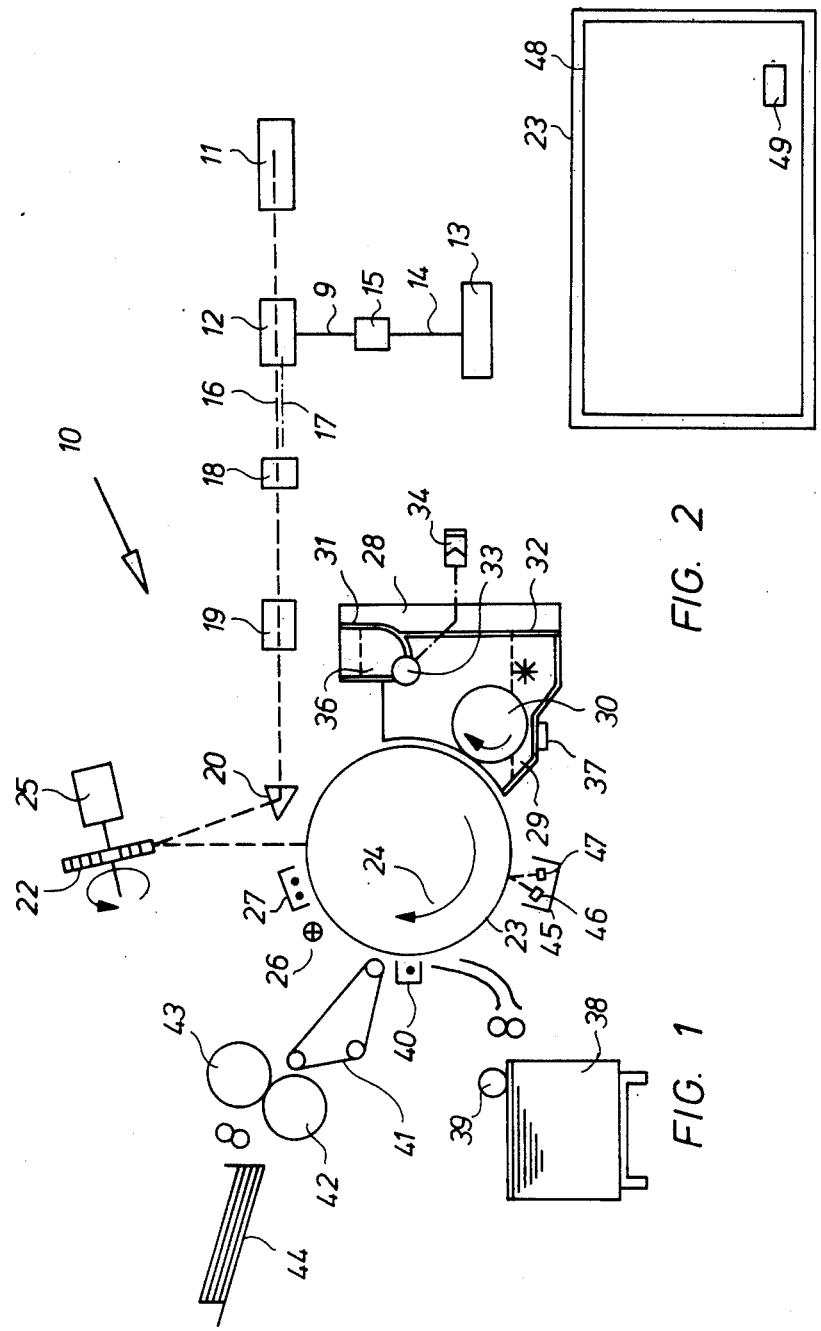

United States Patent [19]

De Wolf et al.

[11] Patent Number: 4,750,838
[45] Date of Patent: Jun. 14, 1988

[54] OPTOELECTRONIC CIRCUIT

[75] Inventors: Alfons J. De Wolf, Ranst; Robert F. Janssens, Geel, both of Belgium

[73] Assignee: Agfa-Gevaert N.V., Mortsel, Belgium

[21] Appl. No.: 920,436

[22] Filed: Oct. 20, 1986

[30] Foreign Application Priority Data

Oct. 30, 1985 [EP] European Pat. Off. ........ 85201758.1

[51] Int. Cl.$^4$ .................... G01N 21/00; G01N 21/47; G01N 21/55
[52] U.S. Cl. .................................. 356/445; 356/434; 356/444; 356/446; 356/448
[58] Field of Search ............... 356/434, 436, 443, 444, 356/445, 446, 448; 250/573, 574

[56] References Cited

U.S. PATENT DOCUMENTS 4,553,033 11/1985 Hubble, III et al. ........... 356/445 X Primary Examiner—Gene Wan
Assistant Examiner—David Mis
Attorney, Agent, or Firm—William J. Daniel

[57] ABSTRACT

An optoelectric circuit for measuring the different optical densities of an image carrier, a toned test patch in an otherwise untoned imaging area of a photoconductor surface in a xerographic apparatus, wherein a LED (46) irradiates a test area of the surface, a phototransistor (47) receives radiation reflected from the text area, an amplifier (51) amplifies the output signal of the phototransistor, the LED is driven by the amplified output current of the phototransistor, and the current through the LED is used as a measure of the optical density.

13 Claims, 2 Drawing Sheets

OPTOELECTRONIC CIRCUIT

The present invention relates to a method of generating signals indicative of image contrast. The invention also relates to an optoelectronic circuit for that purpose.

The invention is applicable for example for measuring the optical density of a toner test patch relative to an untoned area of a photoconductor, e.g. a drum, in a xerographic apparatus.

It is known to generate image contrast signals indicative of the optical density of a toner test patch area relative to an untoned background area by means of an optoelectronic circuit comprising a light-emitting diode (LED) for irradiating the image surface, a photosensor for yielding response signals indicative of the flux or intensity of the radiation reflected from the respective toned and untoned areas, means for amplifying such response signals, sample-and-hold means for sampling and holding the amplified signals, and comparator means for providing an output signal that is representative of the difference in the optical densities of the respective areas.

If the time-spacing between the sampling of the signals to be compared is sufficiently small, then the relative density output signal is largely unaffected by any fluctuations in the output of the light source and in the responsiveness of the photosensor, under the influence of temperature variations, etc.

Relative density measurement as above indicated can be performed with less expensive apparatus than is required for making absolute density measurements and is quite adequate for various purposes e.g. for automatically controlling toner image production in xerographic printing or copying appartus by influencing one or another factor affecting toner deposition, such as the the concentration of toner in a two-component developer composition, the charge level of the photoconductor, the bias voltage on the developer, the condition of the photoconductor, etc.

In the known xerographic image contrast control system, toner-reflected and background-reflected light quanta are impinged on a photodiode and output signals therefrom are compared. If the light intensity differential exceeds a certain value a control signal is generated which adjusts the excitation of the light-source (LED) from a normal pre-set level appropriate for normal requirements (see EPA No. 0 004 573).

A photodiode is not as sensitive as would be desirable for some purposes, but is chosen in view of its linear response.

It is an object of the present invention to provide an image contrast signalling method and apparatus by means of which a linearly responding image contrast signal can be obtained even when using a sensitive non-linearly responding sensor, such as a phototransistor.

According to the present invention there is provided a method of generating an image contrast signal indicative of the relative optical densities of different areas of an image-carrier, wherein each of said areas is irradiated by radiation from a curent energized light-emitting diode, radiation quanta modulated by each of said materials is impinged on sensor means which yields an output current varying in accordance with the optical density of the respective areas, and signals indicative of the optical densities of said materials are compared to obtain a signal indicative of one optical density value relative to the other, charcterised in that a change in the output current from said sensor means in response to a change in the intensity of the modulated radiation impinging thereon automatically causes variation of the energising current to said light-emitting diode and any incident light intensity change occurring within a certain range of flux values is thereby compensated so that the working point of the sensor remains substantially the same; and in that the current level through the light-emitting diode serves as a signal representative of the optical density of the irradiated material.

This method takes advantage of the fact that there is almost a linear relationship betwen the current through a light-emitting diode (LED) and its radiation emission. When making the radiation emission dependent on the optical density of the irradiated material as above specified, the current through the diode can be taken as a measure of that optical density. The invention affords the advantage that the relative density output signal available is infinitely variable with and linearly responsive to relative density. The output signal can be used for image control purposes, e.g. for toner image production control in a xerographic printing or copying apparatus.

Various types of photosensor can be used in carrying out the invention, e.g. a photodiode, a photomultiplier or a phototransistor. It is a particularly important potential advantage of the method, as compared with the prior art relative density signalling method, that use can be made of a photosensor which is much more sensitive than a photodiode. Preferably the photosensor used in a method according to the invention is a phototransistor. The use of such a phototransistor even makes it possible to operate under infrared conditions in order to eliminate the disturbing influence of ambient light.

Where transparent images and image-carriers are concerned, the method according to the invention can be used for signalling the relative image density in transmission, the senor being arranged to receive the radiation passing through the image. In the presently preferred forms of the invention, it is applied for measuring relative image density by detecting and comparing the intensities of reflected light.

The method according to the invention can be applied in a variety of image-production work, e.g. in xerography and in colour photoprinting. In colour photoprinting the method can be used for example for signalling colour correction factors required for producing a satisfactory colour reproduction. For instance the optical density of a given zone of a red colour separation proof print relative to the optical density of the corresponding zone of the original being reproduced can be determined by the method, using a red-light-emitting diode and an appropriate associated sensor, and the relative density output signal can be used to indicate the adjustment which is required to the cyan exposure of the photosensitive material, e.g. by variation of the cyan filter, in order to correct an inaccuracy in the color reproduction. The output signal representing relative density can be used for generating a video display of a correction factor for the guidance of an operator and/or can be used for automatically controlling a colour printer. The method can likewise be used to determine colour correction factors for the other primary colours, using in each case a light-emitting diode with a light output of the appropriate spectral composition. The measurements of the relative densities of the different primary colours can be performed using different apparatus or the different LED/sensor combinations can be integrated into a common apparatus. Such an application of the invention can be very useful for example for establishing the colour balance of a fresh pack of photosensitive copying material. The fact that the spectral composition of the radiation emitted by a LED does not change with change in radiation intensity is a considerable advantage.

One important practical application of the invention is the determination of the optical density of a xerographic toner deposit on a carrier surface, e.g. the surface of a photoconductive drum, relative to an untoned area of such surface, and in particular the determination of the relative optical density of a toner-developed test patch on a photoconductor for the purpose of establishing correct process settings for forming a toner image of a required contrast in a following xerographic print production. In the subsequent description herein of particular features and embodiments of the invention, it will be referred to primarily in that context.

A light-emitting diode is a temperature-dependent light source. The radiation output decreases with increase of the temperature of the diode. It is therefore necessary to measure the optical densities of the toner deposit and untoned background surface within a short lapse of time during which an undesirable temperature change of the diode will not occur. Such a quick succession of the two measurements does not give rise to problems in most xerographic applications since in common xerographic copying apparatus the photoconductor drum rotates at a speed not faster than 10 revolutions per minute. The two successive measurements can easily be performed within a rotation of less than 45 angular degrees, so that it is easy to keep the measuring interval smaller than 1/80th of a second.

The invention includes an optoelectronic circuit having features making it capable of performing a method according to the invention as above defined.

In a circuit according to the invention, the means for determining the current through the light-emitting diode and for using said current as the signal that is representative of the optical density of a toner test patch or other image area, may be a silicon diode that is forwardly biased by the current through the light-emitting diode. The response of such diode in this mode of operation is logarithmic as known in the art, and in this way the output of the circuit may be directly calibrated in relative optical densities, in accordance with the equation:

$$D = \log I_u/I_t$$

wherein:

D is the optical density $I_t$ is the radiation intensity reflected from (or transmitted through as the case may be) a given image or background area (e.g. a toner test patch on a photoconductive surface or an untoned background area of such surface; and $I_u$ is the radiation intensity input In an optoelectronic circuit according to the invention use is preferably made of an optoelectronic component comprising the light-emitting diode and a phototransistor arranged in a common housing in such a way that the phototransistor only receives light from the light-emitting diode if this light has first been reflected from a surface exterior of the housing. Optoelectronic components of that form are compact, cheap and reliable, and they are used on a large scale in automated production processes for the counting of objects that are passed in front of them by suitable conveyor means. In these applications the components operate merely digitally, i.e. they signal the presence or absence of an object, and their non-linear response is of no consequence. The optoelectronic circuit according to the present invention permits the use of these low grade elements for carrying out measurements that are sufficiently accurate for the purpose in view.

Figure 3:
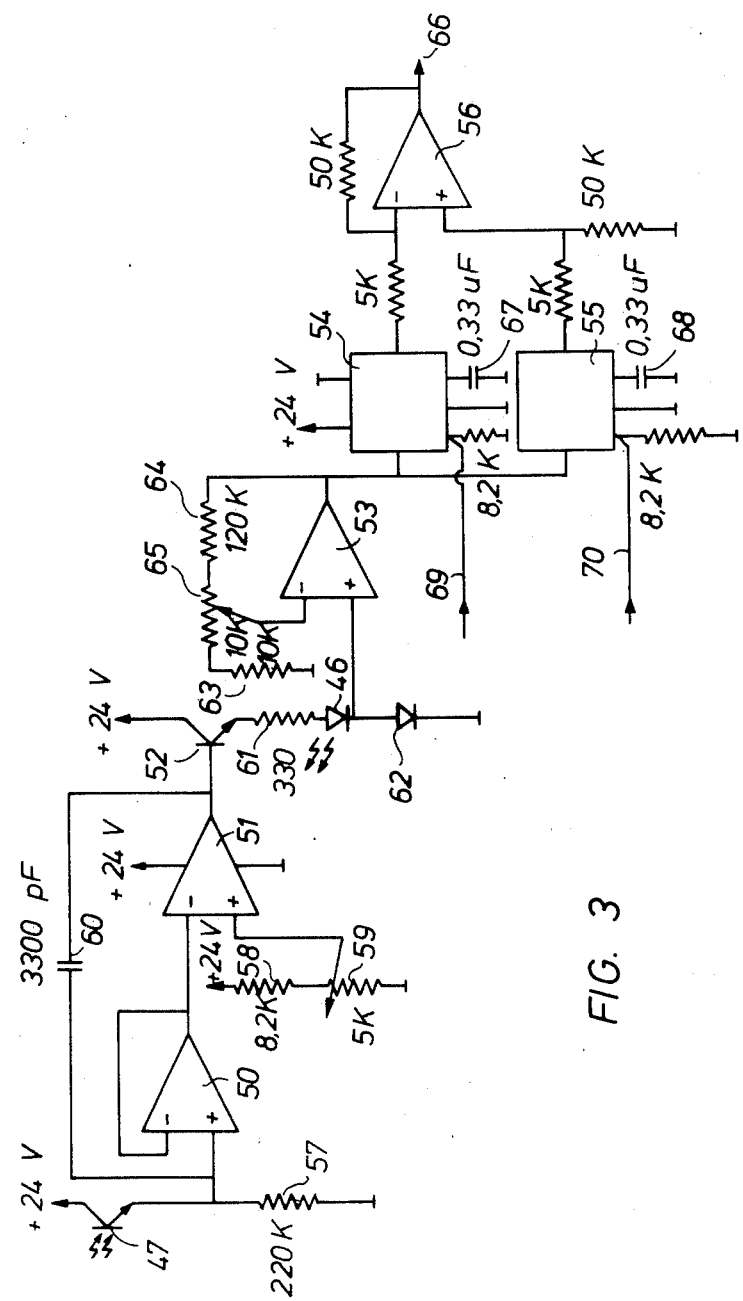

The invention will be described hereinafter by way of example with reference to the accompanying drawings wherein FIG. 1 is a diagrammatic illustration of a laser printer embodying an optoelectronic circuit according to the invention, FIG. 2 represents a developed view of the surface of the photoconductor of the printer, showing the location of a toner-developed test patch within the untoned (background) area of the photoconductor, and FIG. 3 shows the electronic circuit of the device.

FIG. 1 shows a laser-activated xerographic printer generally designated 10. A laser light source 11 transmits a collimated light beam to light beam modulator 12. Signals which designate data bits, ones or zeros, from character generator 13 and which represent portions of alphanumeric characters to be printed by the printer 10 are sequentially transmitted over line 14 to RF (radio frequency) generator 15. If one bit signal is transmitted, RF generator 15 transmits a RF voltage over line 9 to light beam modulator 12, otherwise no RF voltage is transmitted. The individual bit signals are gated or clocked from character generator 13 by a character generator clocking signal.

The light beam modulator 12 may be an acousto-optical modulator which, in response to RF voltages, establishes acoustic vibrations which cause a portion of the input radiation beam to be diffracted through a specific angle along a deflected path. The portion of the deflected beam is called the first order beam 16 while the undeflected beam is called the zero-order beam 17.

The modulated beam is then passed through a negative lens 18 and an adjustable positive lens 19 which together co-operate to control the size and focus of the first order beam. From there, the modulated beam impinges on prism 20, and then upon a multifaceted rotating reflection mirror 22 driven by a motor 25.

Rotating mirror 22 acts on the modulated beam reflecting it towards the photoconducting drum 23 while at the same time causing it to sweep repeatedly in fan-like fashion in one plane, across the surface of the drum. In a preferred embodiment, only the first order beam 16 is enabled to impinge upon the surface of the photoconducting drum 23. Hence, "ones" stored in the character generator memory are transmitted as high bit signals to RF generator 15 which causes RF pulses to be transmitted to light beam modulator 12 which in turn causes first order beam 16 to be switched on. The light impinges on photoconducting drum 23 to image a dot thereon.

Photoconducting drum 23 is caused to rotate in the direction of the arrow 24 while the repeatedly sweeping laser beam traverses a series of parallel straight lines across the surface of the drum. The straight lines are parallel to the axis of the drum.

Rotating mirror 22 is a highly polished multi-faceted mirror rotating several hundreds of revolutions per minute, so that adjacent straight lines traversed on the photoconducting drum 23 may be designed to be approximately 0.0625 mm apart. Since the first order light beam is caused to switch on and off at a RF frequency in the order of magnitude of tens of Megacycles, each straight line path is provided with a large number of possible dot sites, for instance 3456 in a 21 cm straight line segment.

When a first order beam strikes the drum the electrostatically charged drum is locally discharged at the exposure site, so that when a toner having the same charge polarity as that of the initial charge on the drum is applied thereto, the toner deposits on the discharged site and this toner deposit will form a dark dot on the eventual print.

In areas which are not irradiated no toner will adhere to the drum and the corresponding areas of the print will remain white. In this way, alphanumeric characters are printed as a series of dots and no dots in accordance with data bit produced in the characer generator.

The operating cycle of the photoconducting drum is as follows. Prior to the dot-wise exposure, drum 23 is uniformly flooded with light from a source 26 in order to completely discharge the photoconductor after the previous exposure. The photoconducting drum 23 is then uniformly electrostatically charged by corona discharge from a charging station 27.

The dot-wise pattern of discharged sites resulting from the exposure by the laser beam is developed in a developing station 28 containing a two-component developing mixture 29. This mixture is composed of triboelectrically chargeable toner powder and magnetisable carrier particles. The mixture is fed to the developing station by a so-called magnetic brush 30 which is a roller with interior magnets which cause a layer of developer mixture to be pulled upwardly by the roller as the roller rotates in the indicated direction. Also at the developing station there is a toner dispenser comprising a toner tank or hopper 31 mounted above a developer tank 32 for holding toner powder 36. At the lower portion of the hopper 31 there is a discharge opening for the toner and a toner dispensing roller 33 which closely fits into such opening. Stepwise rotation of roller 33 under control of a solenoid 34 causes the roller to remove a controlled amount of powder from the hopper 31 at each angular step, which powder falls by gravity into the tank 32 in which it is mixed with the developer mixture therein by the stirring wheel 35. Finally there may be provided a measuring coil 37 at the bottom of the developer tank for sensing the relative permeability of the developer mixture.

The developed toner image on the drum 23 is transferred to a plain paper sheet fed from a stack 38 of such sheets. In each cycle a dispenser roller 39 removes the upper sheet from the stack, and feeds it in timed sequence towards the drum 23 so that the leading sheet edge coincides with the leading edge of the toner image on the drum. A transfer corona 40 causes the transfer of the toner image of the drum towards the paper sheet. The sheet is then transported by a belt conveyor 41 towards a fixing station where the toner image is fused onto the sheet under the application of heat and pressure by rollers 42 and 43. The prints are finally received in a tray 44.

The optoelectronic component incorporating the sensor is indicated by the numeral 45, and it comprises a light-emitting diode 46 and a phototransistor 47. The incident and reflected radiation beams have been represented as being inclined to a plane radial to the drum, for the sake of clearness, but actually the elements 46 and 47 are mounted co-axially with each other. The phototransistor is mounted centrally in a housing, and the emission of radiation by the light-emitting diode occurs co-axially, around said phototransistor. An inbuilt fiber optic for the phototransistor ensures that no radiation is received on the phototransistor unless it has been reflected on a surface outside the element. The entire optoelectronic component 45 has the size of a common transistor housing. It is an inexpensive component of a type that is commonly used for signalling in a purely digital way, i.e. yes or no, the presence or not of an object in front of it.

In operation of the apparatus for carring out a measurement on a test patch, the light-modulator 12 is controlled by a microprocessor (not illustrated) that controls the different functions of the apparatus in such a way that the photoconductive surface area 48 of the photoconducting drum 23 (see FIG. 2 which represents such surface in flat condition) that has been uniformly charged by the corona 27, is almost completely discharged except for a test patch area 49. Development of the electrostatic charge image at station 29 results in the tonering of the test patch 49. The amount of toner deposited on such patch is subsequently determined by means of the optoelectronic component 45 and the associated electronic circuit that is hereinafter described.

Referring to FIG. 3, the electronic circuit comprises as active elements the voltage follower 50, the amplifier 51, the power output transistor 52, the amplifier 53, the two sample-and-hold circuits 54 and 55, and the differential amplifier 56. A single stabilised power supply circuit of 24 V is provided (not illustrated).

The output current of the phototransistor 47 is detected over a resistor 57 and is applied via the voltage follower 50 to the inverting input of the amplifier 51. The non-inverting input of the amplifier is connected to the series circuit of the resistor 58 and the potentiometer 59 which enables adjustment of the output current of the amplifier 51 as a function of differences in the working characteristics of the light-emitting diode/phototransistor combination. It has been found that the output current may vary up to a factor of 3 and even more, from one such combination to another. This is not surprising in the case of an inexpensive component that is primarily designed for digital operation only. A capacitor 60 is mounted in feedback over the circuit and prevents oscillations.

In the present example the power output transistor 52 is capable of producing at full output a current of 60 mA through the light-emitting diode 46 which, it should be recalled, is mounted together with the phototransistor 47 in the same housing.

In the operation of the circuit, the current through the light-emitting diode increases as the output current of the phototransitor tends to decrease, and vice versa. In other words, the higher the density of the test patch 49, the greater is the emission of the light-emitting diode, and vice versa. The light-emitting diode cannot produce sufficient light to compensate for very high image density values but it is capable of compensating for variations in optical density values within a range adequate for the purposes in view. In general, for measuring the relative density of a toner test patches it is sufficient for the light emission from the LED to compensate for variations in optical density within the range of 0.0 to 1.5 (a factor of approximately 30).

A resistor 61 limits the maximum current through the light-emitting diode. In the absence of such limiting means, the current through the light-emitting diode could reach such high values—if for one reason or another there were no light reflection towards the phototransistor—that the light-emitting diode would be destroyed. The current through the light-emitting diode is a measure of the density of the test patch. This current is converted into a voltage over an impedance, in the present case a diode 62, preferably a silicon diode. The voltage of a silicon diode is a logarithmic function of the current through the diode and in this way the measurement signal is directly translated into an optical density value.

The voltage over the diode 62 is amplified by the amplifier 53, the gain of which is adjustable by means of the combination of the resistors 63, 64 and the potentiometer 65. The adjustment enables the calibration of the circuit in such a way that for instance an output voltage of 5 V at terminal 66 of the circuit corresponds with a measured density of 0.5, a voltage of 15 V corresponds with a density 1.5, etc.

The output voltage of the amplifier 53 is applied in parallel to the two sample-and-hold circuits 54 and 55. These circuits are in fact analog memories, with capacitors 67 and 68 that are charged in accordance with the input voltage on the circuit. The sampling by the circuits is controlled by the application of a sampling voltage pulse through lines 69 and 70. These pulses are preferably produced in such a way that the sampling in circuit 54 occurs for an untoned area of drum 23, i.e., just prior to the passage of the test patch in front of the phototransistor, while the sampling in circuit 55 occurs when the test patch area is in front of the phototransistor. The differential amplifier 56 produces an output signal that is the difference between both logarithmic input signals, and thus the output voltage at terminal 66 is a measure of the relative density of the toned test patch versus the untoned surface of the drum.

Said voltage may be used to directly control the operation of the toner dispensing roller 33. Said voltage may alternatively or additionally be used in combination with other voltages that are representative of certain variables in the process, such as relative humidity, charge level of the photoconductor, etc., to control in an appropriate way the satisfactory operation of the apparatus. The voltage at terminal 66 may also be used in conjunction with the signal produced by a measuring circuit incorporating the measuring coil 37, to control the operation of the toner dispensing roller.

The following components were used in the circuit described hereinbefore:
  phototransistor/light-emitting diode combination: type S 27302 manufactured by SCAN-A-MATIC in Elbridge, N.Y. 13060 USA, and comprising an inbuilt infrared filter,
  amplifiers 50, 51, 53 and 56: integrated in one OP-amp, type LM 324,
  transistor 52: Power Darlington, type BD 677,
  sample-and-hold circuits 54 and 55: type LF 398.

The adjustment of the resistor 59 of the circuit was such that a LED current of 2 mA was obtained for a measurement of an untoned area on the photoconductor drum, i.e. a relative density of 0 (maximum reflection). This situation is not quite correct since a zero current should correspond with a zero density. In the present example this anomaly was a consequence of the simplified power supply of the electronic circuit. If the power supply were to comprise a $+12$ V and a $-12$ V section rather than one 24 V section as used for the present embodiment, then an increased operative range towards the lower densities would be obtained. In the present example, a satisfactory operation was obtained for a density range from 0.5 to 1.5, and for the purposes under consideration this is more than adequate.

The invention is not limited to the particular optoelectronic circuit described hereinbefore. As examples of possible modifications: The phototransistor and the light-emitting diode may be provided as separate units. In that case the circuit can also be used for measuring optical densities in transmission, instead of by reflection. The light-emitting diode may be one that produces light in the visible range of the spectrum, rather than in the IR-range.

The invention need not necessarily be embodied in a laser-activated xerographic printer. It can for example be used in a printer in which the image-wise exposure is effected by means of a LED-array or in a copier in which the photoconductor drum is exposed to the projected image of an original document etc.

An optoelectronic circuit as described may also be used outside the field of electrophotograhy, where it may afford similar advantages including that of compactness on account of the small dimensions of the sensor/LED component.

What is claimed is:

1. In a method of generating an image contrast signal indicative of the relative optical densities of different image areas of an image-carrier, including the steps of irradiating each of said areas by radiation from a light-emitting diode to generate radiation quanta modulated by each of said image areas, receiving said modulated quanta by sensor means which yields an output signal varying in accordance with the optical density of the respective image areas, and comparing output signals from said sensor means for the different areas to obtain a signal indicative of the optical density value of one area realtive to that of the other, the improvement comprising varying the energizing current passing through said light-emitting diode automatically in response to a change in the output signal from said sensor means as a result of a change in the intensity of the modulated radiation incident thereon, whereby any incident change in light intensity occurring within a certain range of such intensity values is thereby compensated so that the working point of the sensor remains substantially the same and the current level output from the light-emitting diode provides a signal representative of the difference in the optical densities of the irradiated areas.

2. A method according to claim 1, wherein the photosensor is a phototransistor.

3. A method according to claim 1, wherein current levels through the light-emitting diode during irradiation of the different areas are converted to voltages and these voltages are compared to obtain a voltage signal indicative of said difference in optical densities.

4. A method according to claim 1, wherein the radiation from said light-emitting diode is reflected by said different image areas onto said sensor means.

5. A methode according to claim 1, wherein the different image areas are constituted respectively by a xerographic toner deposit on a xerographic carrier and an untoned surface area of said carrier whereby the current output signals from said light-emitting diode can be used for establishing correct process settings for forming a toner image of a required contrast in a subsequent xerographic printing process.

6. In an optoelectronic circuit for generating an image contrast signal indicative of the relative optical densities of different image areas of an image-carrier, said circuit comprising a light-emitting diode for emitting a beam of radiation for successively irradiating said different image areas, sensor means for receiving radiation modulated by said different image areas in accordance with the different optical densities thereof and for generating output signals indicative of the different intensities of the thus modulated radiation, sample-and-hold means for sampling and holding the different output signals from said sensor means for said different image areas, and comparator means for comparing the different output signals held by said sample-and-hold means and generating an output signal indicative of the difference in intensities of the modulated radiation, in combination, the improvement comprising amplifying means for effecting inverse mode amplification of said output signals from said sensor means, means for varying the energizing current to said light-emitting diode in accordance with such inversely amplified sensor output signals so that any change which occurs, within a certain range of values, in the intensity of the radiation incident on the sensor means is thereby compensated so that the working point of the sensor means remains substantially the same; and means for applying the varying energizing current through said light-emitting diode during the irradiation of said first and second areas for generation of said sensor output signals for delivery to said sample-and-hold means for comparison of such signals by said comparator means.

7. In an optoelectronic circuit for generating an image contrast signal indicative of the relative optical densities of different image areas on an image carrier which comprises a light-emitting diode impinging light radiation therefrom in turn upon the different image areas, sensor means receiving such light radiation modulated by said image areaa for generating output signals representative of the different optical densities of the image in said areas, and means for comparing the respective output signals from said sensor means to provide an output signal representative of the difference in optical densities of said area, in combination, the improvement comprising amplifying means having an inverting mode input connected to the output of said sensor means and producing an output current; means for applying the output current of said amplifying means to said light-emitting diode thereby to operate said light emitting diode in dependence on the output current of said amplifying means so that, within a given operative range, the working point of the sensor means remains substantially unchanged and thus compensates for a change in the intensity of radiation modulated by said areas as a result of a corresponding change in the radiation emitted by the light-emitting diode; means for determining the current through the light-emitting diode during successive irradiation of said areas by said diode and generating in accordance with the level of such current a signal representative of the optical density of each such area; and said comparing means compares the thus successively generated signals and yields a signal representative of difference in the optical densities of said different image areas.

8. A circuit according to claim 7, wherein said photosensor means is a phototransistor.

9. A circuit according to claim 8, wherein the sensor means comprises a phototransistor which is combined with the light-emitting diode within a common housing.

10. A circuit according to claim 7, wherein said means for determining the current through the light-emitting diode is a silicon diode that is forwardly biased by the current through the light-emitting diode.

11. A circuit according to claim 10, including means for connecting said silicone diode between ground and the non-inverting input of an amplifier whose output is connected to said comparing means.

12. A circuit according to claim 11, wherein said comparator output signal is a voltage signal and including means for adjusting the gain of said amplifier for adjusting the ratio between said output voltage signal of the circuit and the output signals from said sensor means.

13. A xerographic apparatus comprising a photoconductor imaging surface, means for producing on said photoconductor imaging surface a substantially uniformly toned test patch area while leaving a different area untoned, and an optoelectronic circuit for determining the optical density of said test patch relative to the optical density of the untoned area of said surface, said optoelectronic circuit comprising a light-emitting diode impinging light radiation therefrom in turn upon the different image areas, sensor means receiving such light radiation modulated by said image areas for generating output signals representative of the different optical densities of the images in said areas, and means for comparing the respective output signals from said sensor means to provide an output signal representative of the difference in optical densities of said area, in combination, the improvement comprising amplifying means having an inverting mode intput connected to the output of said sensor means and producing an output current; means for applying the output current of said amplifying means to said light-emitting diode thereby to operate said light emitting diode in dependence on the output current of said amplifying means so that, within a given operative range, the working point of the sensor means remains substantially unchanged and thus compensates for a change in the intensity of radiation modulated by said areas as a result of a corresponding change in the radiation emitted by the light-emitting diode; means for determining the current through the light-emitting diode during successive irradiation of said areas by said diode and generating in accordance with the level of such current a signal representative of the optical density of each such area; and said comparing means compares the thus successively generated signals and yields a signal representative of difference in the optical densities of said different image areas.

* * * * *